(12) United States Patent
Finkel et al.

(10) Patent No.: US 7,708,977 B2
(45) Date of Patent: May 4, 2010

(54) METHOD FOR DIAGNOSIS AND TREATMENT OF VASCULAR DISEASE

(75) Inventors: Toren Finkel, Bethesda, MD (US); Jonathan M. Hill, Bethesda, MD (US); Arshed A. Quyyumi, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 448 days.

(21) Appl. No.: 10/534,626

(22) PCT Filed: Nov. 12, 2003

(86) PCT No.: PCT/US03/36317

§ 371 (c)(1), (2), (4) Date: May 11, 2005

(87) PCT Pub. No.: WO2004/045517

PCT Pub. Date: Jun. 3, 2004

(65) Prior Publication Data

US 2006/0057072 A1     Mar. 16, 2006

Related U.S. Application Data

(60) Provisional application No. 60/445,417, filed on Feb. 5, 2003, provisional application No. 60/426,545, filed on Nov. 15, 2002.

(51) Int. Cl.
| | |
|---|---|
| *A61K 49/00* | (2006.01) |
| *A61K 48/00* | (2006.01) |
| *A61K 35/12* | (2006.01) |
| *A61K 35/14* | (2006.01) |
| *G01N 33/53* | (2006.01) |
| *C12N 5/00* | (2006.01) |
| *C12N 5/07* | (2010.01) |
| *A01N 1/02* | (2006.01) |

(52) U.S. Cl. .................... 424/9.1; 435/2; 435/4; 435/7.1; 435/7.2; 435/7.21; 435/325; 435/332; 435/343; 435/373; 435/375; 424/93.2; 424/520; 424/529

(58) Field of Classification Search .................. None
See application file for complete search history.

(56) References Cited

U.S. PATENT DOCUMENTS

| | | | |
|---|---|---|---|
| 4,403,041 A | 9/1983 | Bürk et al. | |
| 6,156,500 A | 12/2000 | Falb | |

OTHER PUBLICATIONS

Scott et al Circulation. 104:491-496, 2001.*

Dimri et al., "A biomarker that identifies senescent human-cells in culture and in aging skin in-vivo," *Proc.Natl. Acad Sci.U.S.A.* 92:9363-9367, 1995.

Geiger, "The aging of lympho-hematopoietic stem cells," *Nature Immunology* 3:329-333, 2002.

Ito et al., "Endothelial progenitor cells as putative targets for angiostatin," *Cancer Res* 59:5875-5877, 1999.

Kaushal et al., "Functional small-diameter neovessels created using endothelial progenitor cells expanded ex vivo," *Nature Med* 7:1035-1040, 2001.

Lin et al., "Origins of circulating endothelial cells and endothelial outgrowth from blood," *J Clin Invest* 105:71-77, 2000.

Peichev et al., "Expression of VEGFR-2 and AC133 by circulating human CD34(+) cells identifies a population of functional endothelial precursors," *Blood* 95:952-958, 2000.

Reyes et al., "Origin of endothelial progenitors in human postnatal bone marrow," *J Clin Invest* 109:337-346, 2002.

Takahashi et al., "Ischemia- and cytokine-induced mobilization of bone marrow-derived endothelial progenitor cells for neovascularization," *Nat Med* 5:434-438, 1999.

Walter et al., "Statin therapy accelerates reendothelialization. A novel effect involving mobilization and incorporation of bone marrow-derived endothelial progenitor cells," *Circulation* 3017-3024, 2002.

Werner et al., "Circulating Endothelial Progenitor Cells and Cardiovascular Outcomes," *N Engl J Med* 353:999-1007, 2005.

Asahara et al., *Science* 275:964-967, 1997.

Asahara et al., *Circulation Research* 85:221-228, 1999.

Asahara et al., *The EMBO Journal* 18(14):3964-3972, 1999.

Bahlmann et al., *Blood* 103(3):921-926, 2004.

Dimmeler et al., *The Journal of Clinical Investigation* 108(3):391-397, 2001.

Eizawa et al., *Current Medical Research and Opinion* 19(7):627-633, 2003.

Gokce et al., *Circulation* 105:1567-1572, 2002.

Grant et al., *Nature Medicine* 8(6):607-612, 2002.

Halcox et al., *Circulation* 106:653-658, 2002.

Hill et al., *The New England Journal of Medicine* 348(7):593-600, 2003.

Kalka et al., *Circulation Research* 86:1198-1202, 2000.

Kocher et al., *Nature Medicine* 7(4):430-436, 2001.

Llevadot et al., *The Journal of Clinical Investigation* 108(3):399-405, 2001.

(Continued)

*Primary Examiner*—Sumesh Kaushal
(74) *Attorney, Agent, or Firm*—Klarquist Sparkman, LLP

(57) ABSTRACT

A method for diagnosing decreased vascular function is disclosed. The method includes assaying the number of endothelial progenitor cells. A method for detecting increased cardiovascular risk is also disclosed, as is a method for diagnosing atherosclerosis. In one example, the methods include assaying the number of endothelial progenitor cells. A method for treating a subject with decreased vascular function is disclosed. The method includes administering a therapeutically effective amount of endothelial progenitor cells to the subject. In one embodiment, the subject has atherosclerosis.

25 Claims, 6 Drawing Sheets

OTHER PUBLICATIONS

Luttun et al., *Trends Cardiovasc Med* 12(2):88-96, 2002.
Murohara et al., *The Journal of Clinical Investigation* 105(11):1527-1536, 2000.
Perticone et al., *Circulation* 104:191-196, 2001.
Powell et al., *Arterioscler Thromb Vasc Biol.* 25:296-301, 2005.
Schächinger et al., *Circulation* 101:1899-1906, 2000.
Seiler et al., *Circulation* 104:2012-2017, 2001.
Shintani et al., *Circulation* 103:2776-2779, 2001.
Suwaidi et al., *Circulation* 101:948-954, 2000.
Vasa et al., *Circulation Research.* 89:e1-e7, 2001.
Vasa et al., *Circulation* 103:2885-2890, 2001.

* cited by examiner

A

B

| Characteristics of the 45 Patients According to the Level of Circulating Endothelial Progenitor Cells* | | | | | |
|---|---|---|---|---|---|
| Characteristic | All Subjects (n=45) | High Cell Count, 28.4±3.0 (n=15) | Intermediate Cell Count, 12.4±0.4 (n=15) | Low Cell Count, 4.7±0.8 (n=15) | P Value† |
| Age – yr | 50±2 | 46±3 | 50±3 | 55±3 | 0.07 |
| Body-mass index | 28±0.6 | 28±1.0 | 27±1.0 | 28±1.0 | 0.80 |
| Glucose – mg/dl | 100±5.0 | 92±3.0 | 101±11.0 | 107±8.0 | 0.09 |
| Total Cholesterol – mg/dl | 200±6.0 | 182±11.0 | 193±11.0 | 226±7.0 | 0.002 |
| Low-density lipoprotein cholesterol – mg/dl | 138±5.0 | 127±9.0 | 131±8.0 | 157±7.0 | 0.02 |
| High-density lipoprotein cholesterol – mg/dl | 48±2.0 | 49±3.0 | 46±2.0 | 50±3.0 | 0.80 |
| Triglycerides – mg/dl | 148±16 | 112±16 | 150±27 | 181±36 | 0.09 |
| Insulin – µU/ml | 16.1±3.0 | 12±2 | 21±8 | 15±3 | 0.46 |
| Hypertension – no. (%) | 10 (22) | 1 (7) | 1 (7) | 8 (53) | 0.01 |
| Diabetes – no. (%) | 10 (22) | 0 | 5 (33) | 5 (33) | 0.04 |
| Smoker – no. (%) | 3 (7) | 1 (7) | 0 | 2 (13) | 1.00 |
| Framingham risk score‡ | 4.2±0.6 | 1.8±0.8 | 4.1±0.8 | 6.6±0.9 | <0.001 |
| Flow-mediated brachial reactivity – % change from base line | 7.8±0.5 | 10.0±0.8 | 8.2±0.8 | 5.2±0.7 | <0.001 |
| Nitroglycerin response – % | 12.6±0.6 | 14.3±1.0 | 12.4±0.9 | 11.3±1.0 | 0.06 |

*Plus-minus values are means ±SE. Body-mass index is the weight in kilograms divided by the square of the height in meters. To convert values for glucose to millimoles per liter, multiply by 0.05551. To convert values for cholesterol to millimoles per liter, multiply by 0.02586. To convert values for triglycerides to millimoles per liter, multiply by 0.01129.
†P values are from a t-test comparison of the highest and lowest cell-count groups. Noncategorical results were verified with the use of nonparametric tests and were adjusted for age. All statiscically significant relations remained significant in subsequent analyses.
‡The Framingham risk score can range from -6 to 19, with higher scores indicating greater cardiovascular risk.

FIG. 6

METHOD FOR DIAGNOSIS AND TREATMENT OF VASCULAR DISEASE

CROSS REFERENCE TO RELATED APPLICATIONS

This is the U.S. National Stage of International Application No. PCT/US2003/036317, filed Nov. 12, 2003, which was published in English under PCT Article 21(2), which in turn claims the benefit of U.S. Provisional Application No. 60/445,417, filed Feb. 5, 2003; and U.S. Provisional Application No. 60/426,545, filed Nov. 15, 2002.

FIELD

This application relates to the field of vascular disease such as atherosclerosis, more specifically to methods for diagnosis of altered vascular function by assessing the number of endothelial progenitor cells. This application also relates to the use of endothelial progenitor cells in the treatment of vascular disease.

BACKGROUND

Cardiovascular disease is a major health risk throughout the industrialized world. Atherosclerosis, the most prevalent of cardiovascular diseases, is the principal cause of heart attack, stroke, and gangrene of the extremities. It is also the principal cause of death in the United States.

Atherosclerosis is a complex disease involving many cell types and molecular factors (for review, see Ross, *Nature* 362:801-809, 1993). The process is believed to occur as a response to insults to the endothelial cell layer that lines the wall of the artery. The process includes the formation of fibrofatty and fibrous lesions or plaques, preceded and accompanied by inflammation. The advanced lesions of atherosclerosis may occlude an artery, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first event that is observed in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDL's are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

The lipid-filled monocytes are termed "foam cells," and are the major constituent of the fatty streak. Interactions between foam cells and the endothelial and SMCs which surround them lead to a state of chronic local inflammation which can eventually lead to smooth muscle cell proliferation and migration, and the formation of a fibrous plaque. Such plaques occlude the blood vessel concerned and restrict the flow of blood, resulting in ischemia.

Ischemia is characterized by a lack of oxygen supply in tissues of organs due to inadequate perfusion. The most common cause of ischemia in the heart is atherosclerotic disease of epicardial coronary arteries. By reducing the lumen of these vessels, atherosclerosis causes an absolute decrease in myocardial perfusion in the basal state or limits appropriate increases in perfusion when the demand for flow is augmented.

The principal surgical approaches to the treatment of ischemic atherosclerosis are bypass grafting, endarterectomy, and percutaneous translumenal angioplasty (PCTA). The latter approach often fails due to restenosis, in which the occlusions recur and often become even worse. This is estimated to occur at an extraordinarily high (30-50%) rate. It appears that much of the restenosis is due to further inflammation, smooth muscle accumulation, and thrombosis. Thus, there remains a need for methods to diagnose and/or treat atherosclerosis.

SUMMARY

Methods for assessing the number of circulating endothelial progenitor cells are disclosed herein. Enumeration of the number of circulating endothelial progenitor cells can be used to detect alterations in vascular function, and can be used to identify agents that affect vascular function. These methods are of use in diagnosing and treating a variety of vascular disorders, including, but not limited to atherosclerosis.

In one embodiment, a method is disclosed herein for diagnosing decreased vascular function in a subject. The method includes assaying the number of endothelial progenitor cells, for example from a blood sample from a subject. A decrease in the number of endothelial progenitor cells in the sample as compared to a control indicates decreased vascular function.

In another embodiment, a method is also disclosed for detecting increased vascular function in a subject. The method includes assaying the number of endothelial progenitor cells, for example from a blood sample from a subject. An increase in the number of endothelial progenitor cells in the sample as compared to a control indicates increased vascular function.

In yet another embodiment, a method for diagnosing future cardiovascular risk, such as the development of atherosclerosis, is disclosed. The method includes assaying the number of endothelial progenitor cells. A decrease in the number of endothelial progenitor cells in the sample as compared to a control indicates increased cardiovascular risk.

A method is disclosed to screen for agents that affect vascular function. The method includes administering a therapeutically effective amount of the agent to a subject, and assessing the number of endothelial progenitor cells in a sample from the subject. An increased number of endothelial progenitor cells in the sample as compared to a control indicates that the agent affects vascular function. A method is also disclosed for screening for agents of use in treating cardiovascular disease. The method includes administering a therapeutically effective amount of the agent to a subject, and assessing the number of endothelial progenitor cells in a sample from the subject. An increased number of endothelial progenitor cells in the sample as compared to a control indicates that the agent is of use for the treatment of the cardiovascular disease.

Also disclosed is a method for treating a subject with decreased vascular function. The method includes administering a therapeutically effective amount of endothelial progenitor cells to the subject. In one embodiment, the subject has atherosclerosis.

A method is disclosed for diagnosing increased cardiovascular risk or decreased vascular function in a subject. The method includes assaying a number of senescent endothelial progenitor cells in a blood sample from the subject, wherein a increase in the number of senescent endothelial progenitor cells in the sample as compared to a control indicates increased cardiovascular risk or decreased vascular function.

In addition, a method is disclosed for screening for an agent of use in treating a cardiovascular disease. The method includes administering a therapeutically effective amount of the agent to a subject, and assessing the number of senescent endothelial progenitor cells in a sample from the subject. A decreased number of endothelial progenitor cells in the sample as compared to a control indicates that the agent is of use in treating the cardiovascular disease.

The foregoing and other features and advantages will become more apparent from the following detailed description of several embodiments, which proceeds with reference to the accompanying figures.

BRIEF DESCRIPTION OF THE FIGURES

FIG. 2A is a set of bar graphs showing the relationship between endothelial progenitor cell colony forming unit (CFU-endothelial progenitor cell) number and individual risk factors including hypertension, diabetes, total cholesterol levels and age. Individual risk factors were defined in accordance with the Framingham guidelines. FIG. 2B is a line graph of the relationship between calculated Framingham risk score and levels of circulating endothelial progenitor cells. Levels of endothelial progenitor cells were expressed as the mean number of colonies per well using at least four separate determinations for each individual.

FIG. 3A is a line graph showing the correlation of endothelial progenitor cell colony counts with measurements of flow mediated brachial reactivity. FIG. 3B is a bar graph of the tertiles based on measured flow mediated brachial reactivity. Significant differences in circulating endothelial progenitor cell levels are demonstrated. FIG. 3C is a bar graph of the levels of endothelial progenitor cells. A correlation is demonstrated with flow mediated brachial reactivity when corrected for endothelial independent vasodilation (flow mediated brachial reactivity/nitroglycerin). p value in panel 3B and 3C is from a t-test comparison of the highest and lowest tertile adjusted for multiple comparisons (n=3) using the Tukey-Kramer procedure. Age adjustment did not alter the calculated p values.

FIG. 6 is a table (Table 1) showing the characteristics of patients (n=45) analyzed according to the tertiles of circulating endothelial progenitor cells (EPCs). †The p value is from a t-test comparison of the highest and lowest tertile. Non-categorized results were verified with non-parametric tests and also underwent age adjustment. All statistically significant relationships retained significance following these analyses.

DETAILED DESCRIPTION

Terms

Figure 1:
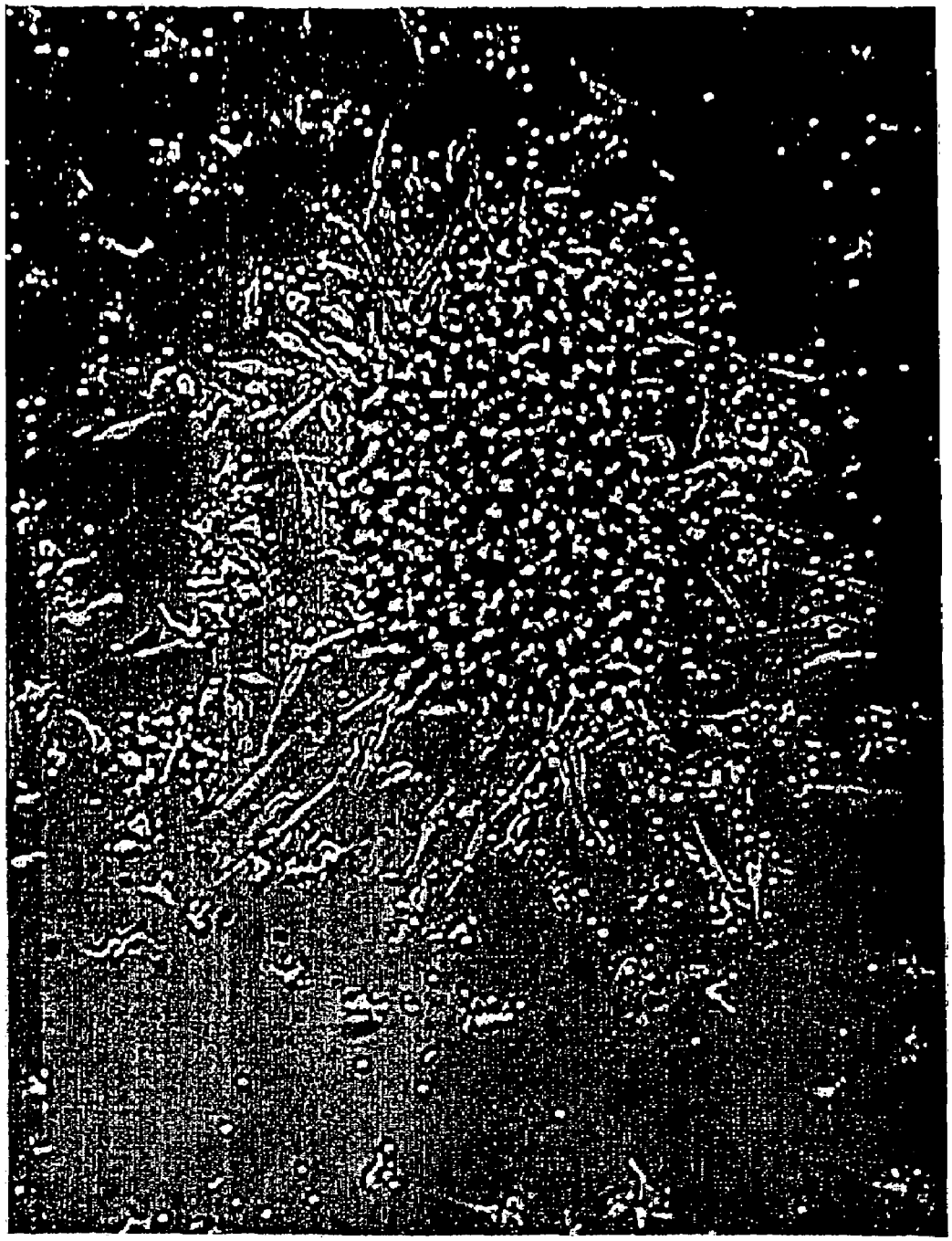
FIG. 1 is a digital image of a phase contrast micrograph of endothelial progenitor cell colony with central cluster of cells surrounded by characteristic spindle shaped cells.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

AC 133 (CD 133): A 120 kDa five transmembrane domain glycoprotein (5-TM) expressed on primitive cell populations, such as CD34 bright hematopoietic stem and progenitor cells, neural and endothelial stem cells, and other primitive cells such as retina and retinoblastoma and developing epithelium. CD133 is expressed on hemagioblasts and developing endothelium, in addition to hematopoietic stem cells and neural stem cells.

Adherent: A cell adheres to a surface if it sticks or clings to the surface. Conversely, a non-adherent cell does not stick to the surface. A non-adherent cell may settle on a surface (for example, due to the forces of gravity), but it can easily be removed from the surface (for example, by gentle agitation).

Atherosclerosis: The progressive narrowing and hardening of a blood vessel over time. Atherosclerosis is a common form of arteriosclerosis in which deposits of yellowish plaques (atheromas) containing cholesterol, lipoid material, and lipophages are formed within the intima and inner media of large and medium-sized arteries.

Blood vessel: The vessels through which blood circulates. In general, blood vessels are elastic tubular channels that are lined with endothelium. Blood vessels include the arteries, veins, and capillaries. Specific, non-limiting examples of a blood vessel include a vena cava, a thoracic aorta, a saphanous vein, a mammary artery, the brachial artery, and a capillary. In another embodiment, a blood vessel includes the smaller arteries and veins. In yet another embodiment, a blood vessel is a capillary of the microvascular circulation.

Brachial-reactivity: The ability of the brachial artery to dilate in response to physiological or pharmacological stimulation. Brachial reactivity is a measure of vascular function or endothelial function. One of skill in the art can readily measure brachial reactivity (see the Examples section below). Previous studies have determined the utility of measuring brachial reactivity as an independent predictor of cardiovascular events.

Buffy coat: A thin yellow or white layer of leukocytes that appears on top of a mass of packed red cells when whole blood is centrifuged.

Cardiovascular: Pertaining to the heart and/or blood vessels.

Cardiovascular risk: The likelihood of the development of disorders related to the cardiovascular system, such as, but not limited to, myocardial ischemia and infarction, intermittent claudication, bowel ischemia, retinal ischemia, transient ischemic attacks, ischemic strokes, and other conditions associated with cardiovascular dysfunction. In a specific non-limiting example, the disorder is myocardial ischemia or infarction.

CD31: A 130 to 140-kdalton single-chain integral membrane glycoprotein that is a member of the immunoglobulin gene superfamily, and is also known as PE-cell adhesion molecule (CAM). The CD31 antigen is composed of six extracellular immunoglobulin-like domains belonging to the C2 group. C2 domains are also found in other members of the immunoglobulin superfamily, the CAMs. The CD31 antigen is expressed on endothelial cells and platelets, T lymphocyte subsets, monocytes, and granulocytes, and is known to function as a vascular cell adhesion molecule and is involved in the process of leukocyte migration through the intercellular junctions of vascular endothelial cells (see Stockinger et al., *J Immunol.* 145(11):3889-3897, 1990).

Cholesterol lowering agent: An agent, such as a pharmaceutical, vitamin, or small molecule, that lowers the level of cholesterol in a subject. One of skill in the art can readily identify assays, such as blood screening, to determine the effect of cholesterol. Agents include, but are not limited to, niacin, the statins (e.g., Zocor™, Lipitor™, Pravacol™, Lescor™, Mevacor™), binding resins (e.g., Questran™), and fibrates (e.g. Lopid™, Lipidil Micro™).

Differentiation: The process by which cells become more specialized to perform biological functions. Differentiation is a property that is often totally or partially lost by cells that have undergone malignant transformation.

Endothelial progenitor cell: A cell that can give rise to a differentiated endothelial cell. In one specific, non-limiting example, endothelial progenitor cells express a number of endothelial specific markers including receptors for vascular endothelial growth factor (VEGFR-2), CD31, Tie-2 and VE-Cadherin (Asahara et al., *Science* 275:964-967, 1997; Peichev et al., *Blood* 95:952-958, 2000).

Endothelial progenitor cells can be isolated from circulating mononuclear cells (Asahara et al., *Science* 275:964-967, 1997; Lin et al., *J Clin Invest* 105:71-77, 2000; Peichev et al., *Blood* 95:952-958, 2000), bone marrow (Reyes et al., *J Clin Invest* 109:337-346, 2002) and cord blood (Murohara et al., *J Clin Invest* 105:1527-1536, 2000). Injection of these cells into animal models with active ischemia results in the incorporation of endothelial progenitor cells into sites of neovascularization (Asahara et al., *Science* 275:964-967, 1997; Murohara et al., *J Clin Invest* 105:1527-1536, 2000; Takahashi et al., *Nat Med* 5:434-438, 1999; Asahara et al., *EMBO J* 18:3964-3972, 1999; Asahara et al., *Circ Res* 85:221-228, 1999; Kocher et al., *Nature Med* 7:430-436, 2001; Grant et al., *Nature Med* 8:607-612, 2002; Luttun et al., *Trends in Cardiovasc Med* 12:88-96, 2002). In one example, these cells also possess a number of endothelial properties including an ability to incorporate modified lipids such as oxidized LDL and to release NO in response to VEGF stimulation (Asahara et al., *Science* 275:964-967, 1997).

"Assaying the number of endothelial progenitor cells" refers to assaying the amount of endothelial progenitor cells in a sample. The assay can be direct (such as counting the cells) or indirect (such as counting the number of colonies grown from the sample). The absolute number of cells in the sample can be determined, or the number of cells can be determined relative to a control. The sample can be a sample from any subject that includes endothelial progenitor cells. Suitable samples include, for example, a whole blood sample or a population of cells isolated from the subject. The number of endothelial progenitor cells can be determined using any method known to one of skill in the art. Exemplary methods are disclosed herein to determine the number of endothelial progenitor cells.

Framingham Risk Score: A risk factor score that is used for predicting future risk of coronary artery disease in individuals free of disease, based on the measurement of risk factors including age, gender, systolic blood pressure, cigarette smoking, glucose intolerance, left ventricular hypertrophy, as well as total cholesterol, low density lipoprotein (LDL) and high density lipoprotein (HDL) levels (Wilson et al., *Am J Cardiol* 59:91G-94G, 1987).

Fibronectin: A dimeric glycoprotein of 430 kD (two chains of a molecular weight of about 250 kD) found in all vertebrates. The two subunits of fibronectin are joined by a pair of disulphide bonds near to their carboxyl termini. Fibronectin is a rod-like molecule composed of three different types of homologous repeating modules that constitute an independently folded unit. All three types of modules are composed exclusively of anti-parallel beta-sheets and turns with no alpha-helix.

All fibronectin modules are highly conserved and are found in a wide array of other proteins. Twelve type-1 modules (approximately 45 amino acids) make up the aminoterminal and carboxy-terminal region of fibronectin. These modules are involved mainly in fibrin and collagen binding. Two type-2 modules (approximately 60 amino acids) are involved in binding collagen. The fifteen type III modules contain an RGD fibronectin receptor recognition sequence along with binding sites for other integrins and heparin.

Fibronectin can serve as a general cell adhesion molecule by anchoring cells to collagen or proteoglycan substrates. Fibronectin plays a role in cell adhesion, cell morphology, and surface architecture.

Granulocyte colony stimulating factor (G-CSF): An O-glycosylated 19.6 kDa glycoprotein with a pI of 5.5. The biologically active form is a monomer. The analysis of its cDNA has revealed a protein of 207 amino acids containing a hydrophobic secretory signal sequence of 30 amino acids. G-CSF contains 5 cysteine residues, four of which form disulfide bonds (positions 36-42; 64-74). The sugar moiety of G-CSF is not required for full biological activity.

Human G-CSF is active in murine cells and vice versa. G-CSF stimulates the proliferation and differentiation of hematopoietic progenitor cells committed to the neutrophil/granulocyte lineage in a dose-dependent manner. At higher concentrations this factor induces the generation of colonies in soft agar cultures containing granulocytes and macrophages. The fully differentiated neutrophilic granulocytes are functionally activated by G-CSF.

Granulocyte/macrophage colony-stimulating factor (GM-CSF): GM-CSF is a monomeric protein of about 127 amino acids with two glycosylation sites. The protein is synthesized as a precursor of about 144 amino acids, which includes a hydrophobic secretory signal sequence at the aminoterminal end. The human gene has a length of approximately 2.5 kb and contains four exons. The distance between the GM-CSF gene and the IL-3 gene is approximately 9 kb. The human GM-CSF gene maps to chromosome 5q22-31.

GM-CSF was isolated initially as a factor stimulating the growth of macrophage/granulocyte-containing colonies in soft agar cultures. GM-CSF is also involved in the growth and development of granulocyte and macrophage progenitor cells. It stimulates myeloblasts and monoblasts and triggers irreversible differentiation of these cells. GM-CSF synergizes with erythropoietin in the proliferation of erythroid and megakaryocytic progenitor cells.

GM-CSF has been used clinically for the physiological reconstitution of hematopoiesis in diseases characterized either by an aberrant maturation of blood cells or by a reduced production of leukocytes. In one example, the dose, route and schedules for GM-CSF are 5-10 micrograms/kg/day either by 4-6 hours intravenous infusion or by subcutaneous injection.

GM-CSF has also been used clinically to promote collateral vessel growth. In another example, GM-CSF is administered by intravascular injection of about 10 to about 50 µg, such as about 40 µg. In yet another example, GM-CSF is administered subcutaneously at about 5 to 20 µg/kg, or at about 10 µg/kg (see also Seiler et al., *Circulation* 104(17):2012-7, 2001).

Growth Factor: A "growth factor" is a substance that affects the growth of a cell or organism. In general, growth factors stimulate cell proliferation or maturation when they bind to their receptor ("growth factor receptor"). In one embodiment, growth factors are a complex family of polypeptide hormones or biological factors that control growth, division and maturation of hematopoietic cells. In another embodiment, growth factors regulate the division and proliferation of cells and influence the growth rate of neoplastic tissue (e.g. cancers). A growth factor can be a naturally occurring factor or a factor synthesized using molecular biology techniques. In one specific, non-limiting example, a growth factor can be used stimulate to lymphocyte production or differentiation, and thus can be used following chemotherapy or bone marrow transplantation.

Leukocyte: Cells in the blood, also termed "white cells," that are involved in defending the body against infective organisms and foreign substances. Leukocytes are produced in the bone marrow. There are 5 main types of white blood cell, subdivided between two main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B cell and T cells.

Maturation: The process in which an immature cell, such as a precursor cell, changes in form or function to become a functional mature cell, such as a mature T or B cell.

Mobilization Agent: A compound such as a naturally occurring protein or a derivative thereof, that acts on endothelial progenitor or stem cells to mobilize endothelial precursor cells. A mobilizing agent causes endothelial cell precursors to migrate from their tissue of origin such as the bone marrow, and move into other tissues or the peripheral blood. Specific, non-limiting examples of a mobilizing agent are GM-CSF, G-CSF, and AMD-3100 (Anormed, British Columbia, dosing information available on the Anormed website).

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation).

Progenitor cell: A "progenitor cell" is a cell that gives rise to progeny in a defined cell lineage. An "endothelial progenitor cell" is a cell that gives rise to cells of the endothelial lineage. In one specific, non-limiting example, an endothelial progenitor cell is a $VDGRR2^+CD31^{hi}$ cell. A "circulating endothelial progenitor cell" is an endothelial progenitor cell found circulating in the body, such as endothelial progenitor cells in the blood.

Purified: The term "purified" does not require absolute purity; rather, it is intended as a relative term. Thus, for example, a purified cell preparation is one in which the cell referred to is more pure than the cell in its natural environment within a tissue. In one embodiment, a "substantially purified" population of a specific cell type is a composition of cells that includes less than about 20%, less than about 15%, or less than about 10% of cells of a different phenotype. Thus, a substantially purified population of cells includes greater than 80%, greater than 85%, or greater than 90% of the cells of interest. In another embodiment, a process that produces a purified population of cells is a process that produces a population of cells so that more than 50% of the resulting population is the cell type of interest.

Senescence: A state of a cell in which the cell reaches the end of its proliferative capacity and is unable to undergo subsequent cell division. A senescent cell is still viable, but does not divide.

Subject: Any subject that has a vascular system and has hematopoietic cells. In one embodiment, the subject is a non-human mammalian subject, such as a monkey, mouse, rat, rabbit, pig, goat, sheep or cow. In another embodiment, the subject is a human subject.

Therapeutically effective amount of a cell: An amount of a endothelial progenitor cell, that can be determined by various methods, including generating an empirical dose-response curve, predicting potency and efficacy by using modeling, and other methods used in the biological sciences. In general, a therapeutically effective amount of endothelial progenitor cell is an amount sufficient to improve vascular function. In one specific, non-limiting example, a therapeutically effective amount of an endothelial progenitor cell is an amount sufficient to treat atherosclerosis, or to delay or prevent an ischemic event. In one embodiment, a therapeutically effective amount of a endothelial progenitor cell is more than about 10,000 cells, more than about 20,000 cells, more than about 30,000 cells, or between about 5,000 cells and about 50,000 cells.

The therapeutically effective amount of cells will be dependent on the subject being treated (e.g. the species or size of the subject), the degree that the vascular function is impaired in a subject, and the location of the survival of the transplanted cells in the subject.

Specific assays for determining the therapeutically effective amount of endothelial cells are provided herein. The methods disclosed have equal application in medical and veterinary settings. Therefore, the general term "subject being treated" is understood to include all animals (e.g. humans, apes, dogs, cats, mice, rats, rabbits, sheep, pigs and cows) and vascular function is monitored using the assays described herein.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transplantation: The transfer of a tissue or an organ, or cells, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or cells from one location to another in the same individual, or transplantation of a tissue or cells from one individual to another, wherein the two individuals are genetically identical.

Vascular function: The function of the blood vessels. Decreased vascular function is associated with atherosclerosis, myocardial infarction, intermittent claudication, bowel ischemia, retinal ischemia, transient ischemic attacks (TIAs), ischemic strokes, restenosis after angioplasty, transplant atherosclerosis, unstable angina, sudden death, and alterations in blood pressure.

Vascular function assessment: An assay that measures the function of the vascular system. Assays include measurement of a parameter of the blood, assays of arterial hyperplasia, vascular contractility measurements, brachial reactivity measurements, and morphometric measurements. Similarly, an endothelial cell assessment is a test that measures a function or parameter of an endothelial cell. "Decreased vascular function" indicates a decrease in any function of the blood vessels, as compared to a standard value or a control sample. Thus, in one example, decreased vascular function is a decrease in a vascular contractility, as compared to a known value for normal vascular contractility. In another example, decreased vascular function is the lower contractility of a blood vessel as compared to the contractility of a vessel known to not be affected by as a disease or a disorder. In a further example, decreased vascular function is a lower vascular contractility as compared to the contractility of a vessel from the same subject at an earlier time point.

Vascular tissue: Tissue consisting of, or containing, vessels as an essential part of a structure. Vascular tissue operates by means of, or is made up of an arrangement of, vessels. Vascular tissue includes the arteries, veins, capillaries, lacteals, microvasculature, etc. In one embodiment, vascular tissue includes a highly vascularized organ (e.g. the lung). In another embodiment, vascular tissue is a blood vessel, or a portion thereof. Cells isolated from a vascular tissue are a population of cells isolated from the remaining components of the tissue. One specific, non-limiting example of cells from a vascular tissue are endothelial cells isolated from vascular tissue, such as a blood vessel.

Vascular Endothelial Growth Factor (VEGF): VEGF is a homodimeric heavily glycosylated protein of 46-48 kDa (24 kDa subunits). Glycosylation is not required, however, for biological activity. The subunits are linked by disulfide bonds. The human factor occurs in several molecular variants of 121 (VEGF-121), 165 (VEGF-165), 183 (VEGF-183), 189 (VEGF-189), 206 (VEGR-206) amino acids, arising by alternative splicing of the mRNA (for review see Neufeld et al., *FASEB J.* 13: 9, 1999)

The human gene encoding VEGF has a length of approximately 12 kb and contains eight exons. Four species of mRNA encoding VEGF have been identified and found to be expressed in a tissue-specific manner. They arise from differential splicing with the 165 amino acid form of VEGF lacking sequences encoded by exon 6 and the 121 amino acid form lacking exon 6 and 7 sequences. The VEGF gene maps to human chromosome 6p12-p21.

VEGF is a highly specific mitogen for vascular endothelial cells. In vitro the two shorter forms of VEGF stimulate the proliferation of macrovascular endothelial cells. VEGF does not appear to enhance the proliferation of other cell types. VEGF significantly influence vascular permeability and is a strong angiogenic protein in several bioassays and probably also plays a role in neovascularization under physiological conditions. A potent synergism between VEGF and beta-FGF in the induction of angiogenesis has been observed. It has been suggested that VEGF released from smooth muscle cells and macrophages may play a role in the development of arteriosclerotic diseases.

VEGF can be assayed by an immunofluorometric test. An alternative and entirely different detection method is RT-PCR quantitation of cytokines. Methods for performing these assays are known (e.g. see Yeo et al., *Clinical Chem.* 38:71, 1992).

VEGF receptor: A receptor found on the surface of a cell that specifically binds VEGF. VEGF receptors are high-affinity glycoprotein receptors of 170-235 kDa. VEGF receptors are expressed on vascular endothelial cells. The interaction of VEGF with heparin-like molecules of the extracellular matrix is required for efficient receptor binding. Protamine sulfate and suramin are capable of replacing the receptor-bound factor. The high-affinity receptor for VEGF, now known as VEGF-R1, has been identified as the gene product of the flt-1 gene.

Another receptor for VEGF, now known as VEGF-R2, is KDR, also known as flk-1. This receptor is a receptor tyrosine kinase. The human gene maps to chromosome 4q31.2-q32 and encodes a transcript of approximately 7 kb. It has been shown that VEGF-R2 (flk-1) is expressed abundantly in proliferating endothelial cells of the vascular sprouts and branching vessels of embryonic and early postnatal brain and that its expression is reduced drastically in adult brain where proliferation has ceased. Flk-1 is expressed also in the blood islands in the yolk sac of embryos. The expression of this receptor therefore correlates with the development of the vascular system and with endothelial cell proliferation. (See Joukov et al., *EMBO J.* 15:290-298, 1996).

Vector: In one embodiment a nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. In one embodiment the term "vector" includes viral vectors, such as adenoviruses, adeno-associated viruses, vaccinia, and retroviral vectors. In one embodiment the term vector includes bacterial vectors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Diagnosis

A method of diagnosing vascular function in a subject is disclosed herein. Specifically, the method is of use in diagnosing decreased vascular function. In several embodiments, the method includes assaying endothelial progenitor cells. The assay can determine endothelial cell (or endothelial precursor cell) function, endothelial cell activity, or can determine the number of circulating endothelial cells.

The method can be used, for example, to predict future cardiovascular risk. Specifically, the method can be used to predict risk for myocardial infarction, intermittent claudication, bowel ischemia, retinal ischemia, transient ischemic attacks (TIAs), ischemic strokes, restenosis after angioplasty, transplant atherosclerosis, unstable angina, sudden death, and other conditions associated with cardiovascular dysfunction. In one specific, non-limiting example, the enumeration of endothelial progenitor cells is of use in predicting cardiovascular risk for myocardial ischemia and/or infarction. Cardiovascular risk indicates the potential for a future cardiovascular event, such as myocardial infarction, intermittent claudication, bowel ischemia, retinal ischemia, transient ischemic attacks (TIAs), ischemic strokes, restenosis after angioplasty, transplant atherosclerosis, unstable angina, sudden death, and other conditions associated with cardiovascular dysfunction. Factors involved in cardiovascular risk include, but are not limited to, serum cholesterol, hypertension, diabetes, sex, and age.

In another specific, non-limiting example, the enumeration of endothelial progenitor cells is of use in diagnosing atherosclerosis. Thus, the method includes measuring the number of circulating endothelial cell precursors to determine the risk for developing a cardiovascular condition such as, but not limited to, atherosclerosis.

The methods disclosed herein include assaying the number of endothelial progenitor cells. A decrease in the number of endothelial progenitor cells as compared to a control indicates decreased vascular function, for example, increased future cardiovascular risk. In one specific, non-limiting example, an assessment of the risk of a subject to develop vascular disease, or an assessment of vascular function is made by determining the number of circulating endothelial progenitor cells, using methods such as the ones disclosed below.

In one embodiment, assaying the number of endothelial progenitor cells includes isolating the buffy coat from a blood sample of the subject and culturing the buffy coat on a solid support coated with a substrate, including, but not limited to fibronectin, vitronectin, or collagen. In one specific, non-limiting example, the solid substrate, such as a polymer suitable for tissue culture, is coated with fibronectin. The culture period can be from about 24 hours to about 72 hours, such as but not limited to, for about 36 hours or about 48 hours. The non-adherent cells are isolated from the culture and again cultured on a solid support coated with a substrate. The substrate includes, but is not limited to, fibronectin, vitronectin, or collagen. The substrate can be the same as used for the culture of the buffy coat, or can be different. In one example, the substrate is fibronectin for both the culture of the buffy coat and the culture of the non-adherent cells. Solid surfaces suitable for tissue culture are known in the art, and include, but are not limited to, polystyrene, glass, and polypropylene.

The number of colonies produced on the solid support is then enumerated. For example, enumeration can take place at 4 to 10 days following culture of the non-adherent cells. In one specific, non-limiting example, the number of colonies are counted at about seven days following the plating of the non-adherent cells. In one embodiment, a lower number of colonies on the solid support as compared to a control indicates decreased vascular function or increased cardiovascular risk.

In one specific, non-limiting example, the control is a standard value. In another specific, non-limiting example, the control is the number of colonies obtained after culturing a similar number of cells from the buffy coat of a subject known not to be affected by a specific disease or disorder. In yet another example, the control is the number of colonies obtained from culturing a similar number of cells from the buffy coat of the same subject, taken at a different time, such as an earlier time point.

In another embodiment, the number of circulating endothelial progenitor cells in a subject is evaluated by measuring the number of circulating cells in a sample, such as a blood sample, from the subject. For example, the number of VEGFR2$^+$CD31$^{hi}$ cells is assessed. Alternatively, the number of endothelial progenitor cells expressing AC133 is assessed. One of skill in the art can readily determine the number of these cells. Suitable methods include, but are not limited to, fluorescence activated cell sorting and immunohistochemical staining of blood cells.

Methods of determining the presence or absence of a cell surface marker, such as a VEGF receptor, e.g. VEGFR2, are well known in the art. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals,* 1992-1994. The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionuclides, including, but not limited to, $^{14}$C, $^{3}$H and $^{35}$S.

Fluorescence activated cell sorting (FACS) can be used to sort cells that express VEGFR2, by contacting the cells with an appropriately labeled antibody. In one embodiment, additional antibodies and FACS sorting can further be used to produce substantially purified populations of CD31 expressing (CD31$^{hi}$) cells.

A FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells. (For exemplary methods of FACS see U.S. Pat. No. 5,061,620, herein incorporated by reference). Similarly, FACS can be used to substantially purify VEGFR2 expressing cells, or VEGFR2$^+$CD31$^{hi}$ cells.

However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g. VEGFR2 or CD31) to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support, or fluorochromes, which can be used with a fluorescence activated cell sorter (FACS), to enable cell separation (see above).

In one specific, non-limiting example, the VEGFR2$^+$ CD31$^{hi}$ cells initially may be separated from other cells by the cell-surface expression of CD31. In one specific, non-limiting example, CD31$^{hi}$ cells are positively selected by magnetic bead separation, wherein magnetic beads are coated with CD31 reactive monoclonal antibody. The CD31$^{hi}$ cells are then removed from the magnetic beads.

Release of the CD31$^{hi}$ cells from the magnetic beads can be effected by culture release or other methods. Purity of the isolated CD31$^{hi}$ cells is then checked with a flow cytometer, such as a FACSCAN™ flow cytometer (Becton Dickinson, San Jose, Calif.), if so desired. In one embodiment, further purification steps are performed, such as FACS sorting the population of cells released from the magnetic beads, such as the cells expressing VEGFR2.

In one embodiment, magnetic bead separation is used to first separate a population of cells that do not express more than one lineage specific markers, for example, CD31 or VEGFR2. In addition, panning can be used to separate cells that do not express one or more lineage specific markers. Panning methods are well known in the art (e.g., see Small et al., *J Immunol Methods* 167(1-2):103-7, 1994).

In yet a further embodiment, a function parameter of endothelial cells or endothelial progenitor cells is assessed. Specific, non-limiting examples of these parameters are uptake of acetylated LDL or production of nitric oxide (NO) in response to VEGF stimulation.

In yet another embodiment, a method is provided for diagnosing decreased vascular function or increased risk for cardiovascular disease in a subject that includes determining the number of senescent circulating endothelial progenitor cells in the subject. An increase in the number of senescent circulating endothelial progenitor cells as compared to a control indicates that the subject has decreased vascular function or is at increased risk for the development of a cardiovascular disease.

In one specific, non-limiting example, the control is a standard value. In another specific, non-limiting example, the control is the number of senescent endothelial cells in a subject known not to be affected by a specific disease or disorder. In yet another example, the control is the number of senescent cells from same subject, taken at a different time, such as, but not limited to, an earlier time point when the subject is known to have adequate vascular function.

Methods of isolating endothelial progenitor cells are disclosed herein. Once these cells are isolated, senescence can be measured by any means known to one of skill in the art. For example, endogenous cellular β-galactosidase activity can measured as a marker of cellular senescence (Dimri et al., *Proc. Natl. Acad. Sci. U.S.A.* 92:9363-9367, 1995). Alternatively, cell proliferation can be measured using standard assays such as bromodeoxyuridine (BrdU) or $^3$H-thymidine labeling of cells. In these assays, proliferation of the endothelial progenitor cells results in incorporation of the label.

Drug Screening

A method is disclosed herein for screening agents that can be used to treat cardiovascular disease, or that affect endothelial cell function. The method includes treating a subject with the agent, and assaying for the number of circulating endothelial precursor cells or for a function of endothelial cells or endothelial cell precursors. An increase in the number of endothelial progenitor cells, as compared to a control, indicates that the agent is of use in treating cardiovascular disease or increasing vascular function. In one specific, non-limiting example, the number of senescent endothelial progenitor cells is assessed.

The animal can be any subject, including both human and non-human subjects. In several non-limiting examples, the animal is a primate (human, chimpanzee, macaque, etc.), farm animal (cow, pig, etc.), a domestic animal (cat, dog, etc.), or a rodent (mouse, rat, guinea pig, etc). In one specific, non-limiting example, the subject is a human subject.

In one specific, non-limiting example, the method includes assaying the number of endothelial progenitor cells. An increase in the number of circulating endothelial progenitor cells as compared to a control indicates that the agent is effective for treating a cardiovascular disease, or for increasing endothelial cell function. Suitable controls include an animal not treated with an agent, or a standard value. Suitable controls also include the number of endothelial progenitor cells in the animal prior to treatment with the agent. In several embodiments, the agent is of use in the treatment of myocardial infarction, intermittent claudication, bowel ischemia, retinal ischemia, transient ischemic attacks (TIAs), ischemic strokes, restenosis after angioplasty, transplant atherosclerosis, unstable angina, sudden death, and other conditions associated with cardiovascular dysfunction.

Assaying the number of endothelial progenitor cells includes, for example, isolating the buffy coat from a blood sample of the treated animal and culturing the buffy coat on a solid support coated with a substrate, such as, but not limited to, fibronectin, vitronectin, or collagen. In one specific, non-limiting example, the solid substrate, such as a polymer suitable for tissue culture, is coated with fibronectin. The non-adherent cells are isolated and cultured on a solid support coated with a substrate, such as, but not limited to, fibronectin. The number of colonies produced on the solid support is then enumerated. In one embodiment, a higher number of colonies on the solid support as compared to a control indicates that the agent is effectively increasing endothelial cell function. Thus, a higher number of colonies indicates that the agent is of use in treatment of a cardiovascular disease, and/or for increasing vascular function (see above).

In another embodiment, the number of endothelial progenitor cells in a subject is evaluated by measuring the number of circulating cells in a sample, such as a blood sample, from the subject. For example, the number of VEGFR2$^+$ CD31$^{hi}$ cells is assessed. Alternatively, the number of endothelial progenitor cells expressing AC133 is assessed. Methods for enumerating these cells are described above.

In another specific, non-limiting example, the method includes treating a subject with the agent, and assaying for the number of senescent endothelial precursor cells. A decrease in the number of senescent endothelial progenitor cells, as compared to a control, indicates that the agent is of use in treating cardiovascular disease or increasing vascular function. Methods for determining the number of senescent endothelial cells are disclosed herein.

Examples of agents of interest include, but are not limited to, chemical compounds; growth factors; peptidomimetics; antibodies; synthetic ligands that endothelial cells or endothelial progenitor cells, cytokines, small molecules, and receptor ligands (e.g. agonists of a receptor, such as but not limited to, VEGFR2). The determination and isolation of ligand/compositions is well described in the art. See, e.g., Lerner, *Trends Neuro Sci.* 17:142-146, 1994.

The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad. Sci. U.S.A.* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229-237, 1988).

Methods of Treatment

Methods are disclosed herein for improving vascular function in a subject. The methods include administering to the subject a therapeutically effective amount of endothelial precursor cells, to improve vascular function. In one embodiment, the subject has atherosclerosis. In other embodiments, the subject has had a myocardial infarction, or has intermittent claudication, bowel ischemia, retinal ischemia, transient ischemic attacks (TIAs), ischemic strokes, restenosis after angioplasty, transplant atherosclerosis, unstable angina, or another condition associated with cardiovascular dysfunction.

A therapeutically effective amount of an endothelial progenitor cell can determined by various methods, including generating an empirical dose-response curve, predicting potency and efficacy of using modeling, and other methods used in the biological sciences. In general, a therapeutically effective amount of an endothelial progenitor cell is an amount sufficient to prevent, treat, reduce, eliminate and/or ameliorate a symptom and/or the underlying causes of the disease or disorder being treated, such as any condition associated with cardiovascular dysfunction. In one embodiment, a therapeutically effective amount is an amount sufficient to increase blood flow.

The therapeutically effective amount of endothelial progenitor cells will be dependent on the subject being treated (e.g. the species or size of the subject), the type of cardiovascular dysfunction suffered by the subject, and the location of administration of the cells (e.g. intravenously, locally, etc).

In one embodiment, a therapeutically effective amount of cells is an amount of cells sufficient to treat a subject suffering from a myocardial injury. In specific, non-limiting examples, a therapeutically effective amount of endothelial progenitor cells is more than about 100 cells, more than about 1000 cells, more than about 10,000 cells, more than about 100,000 cells, more than about 250,000 cells, more than about 1,000,000 cells, or between about 250,000 cells and about 1,000,000 cells. In one example, greater than $2 \times 10^6$/kg of endothelial progenitor cells are administered to the subject. In another embodiment, $2 \times 10^6$/kg-$5 \times 10^6$/kg endothelial progenitor cells are administered. Without being bound by theory, these doses of endothelial cells are applicable in both autologous and allogeneic settings (Sezer et al., *J. Clin. Onc.* 18:3319-3320, 2000; Mavroudis et al., *Blood* 88:3223-3229, 1996). Accordingly, it is anticipated that the administration of compositions comprising an equivalent or greater number of endothelial progenitor cells, either alone or in combination with other stem/progenitor cells, should result in increased vascular function and/or decreased cardiovascular risk. Specific assays for determining the therapeutically effective amount of endothelial progenitor cells are provided herein. The methods have equal application in medical and veterinary settings.

In a further embodiment, other agents such as growth factors or cytokines are administered in conjunction with endothelial progenitor cells. For example, a therapeutically effective amount of vascular endothelial growth factor, angiopoeitin, or fibroblast growth factor is administered in conjunction with a therapeutically effective amount of endothelial progenitor cells. These agents can be administered before, after, or simultaneously with the endothelial progenitor cells. One or multiple doses can be administered.

Thus a therapeutically effective amount of endothelial progenitor cells is administered to a subject requiring treatment, such a subject with impaired vascular function. A therapeutically effective amount of endothelial progenitor cells is the amount sufficient to improve vascular function. The composition can be supplemented with growth factors or with other lineage-uncommitted cells. Precise, effective quantities can be readily determined by those who are skilled in the art and will depend, of course, upon the exact condition being treated by the particular therapy being employed. One or multiple doses can be administered. Administration can be systemic or local, and can be by any route, such as intramuscular, subcutaneous, intravascular, intraperitoneal, intranasal, or oral administration. Administration can be by injection. Specific, non-limiting examples of administration by injection include administration by subcutaneous injection, intramuscular injection, or intravenous injection. If administration is intravenous, an injectible liquid suspension of endothelial progenitor cells can be prepared and administered by a continuous drip or as a bolus.

One specific, non-limiting example of local administration is intra-cardiac injection. For intra-cardiac injection, the endothelial progenitor cells are in an injectible liquid suspension preparation or in a biocompatible medium which is injectible in liquid form and becomes semi-solid at the site of damaged myocardium. A conventional intra-cardiac syringe or a controllable endoscopic delivery device can be used so long as the needle lumen or bore is of sufficient diameter (e.g. 30 gauge or larger) that shear forces will not damage the endothelial progenitor cells.

In one specific, non-limiting example, a therapeutically effective amount of endothelial progenitor cells is administered to a subject with impaired vascular function. The endothelial progenitor cells are administered in conjunction with a therapeutically effective amount of a mobilization agent, such as, but not limited to, a therapeutically effective amount of granulocyte macrophage colony stimulating factor (GM-CSF), AMD-3100, or granulocyte colony stimulating factor (G-CSF). In one embodiment, endothelial progenitor cells are administered in conjunction with a mobilizing agent, such as but not limited to, G-CSF or GM-CSF. Administration can be by any route, such as, but not limited to, intracardiac injection (e. g. see Selier et al., *Circulation* 104(17):2012-7, 2001).

The invention is illustrated by the following non-limiting Examples.

EXAMPLES

Example 1

Methods

Study Subjects: Forty-five healthy male subjects >21 years of age (mean 50.3±1.7), with or without conventional cardiovascular risk factors, were studied. Patients were solicited from the community through the NIH Patient Recruitment and Public Liaison Office by placement of a general announcement for volunteers with or without cardiovascular risk factors who were free of ischemic symptoms or a known history of cardiovascular disease. The total risk factor burden was calculated by employing the Framingham risk factor score that has been previously used for predicting future risk of coronary artery disease in individuals free of disease, based on the measurement of risk factors including age, gender, systolic blood pressure, cigarette smoking, glucose intolerance, left ventricular hypertrophy, as well as total cholesterol, low density lipoprotein (LDL) and high density lipoprotein (HDL) levels (Wilson et al., *Am J Cardiol* 59:91G-94G, 1987).

Subjects with known or symptomatic cardiovascular disease were excluded from this study because of the confounding effects of ischemia and corresponding neovascularization on endothelial progenitor cell activity. Similarly, women were excluded from this study because of the potential confounding effects of follicular and uterine wall angiogenesis that occurs during the menstrual cycle. (Masuda et al., *Circulation* 100:475, 1999; Masuda et al., *Circulation* 100:691-692, 1999.) To avoid other conditions in which adult neovascularization might be present, patients with cancer, proliferative retinopathy, hyperthyroidism, or chronic disease were also excluded. All enrolled subjects underwent detailed cardiovascular risk assessment after signing informed consent and the study was approved by the National Heart, Lung, and Blood Institutional Review Board.

No medications, including vitamins, were taken for at least one week prior to the study. Statins and angiotensin converting enzyme (ACE) inhibitors were discontinued for two months after appropriate tapering, and other anti-hypertensive medications were discontinued for at least two weeks with appropriate blood pressure monitoring. Diabetics continued their regular glucose control medications.

Endothelial progenitor cell isolation and colony forming assay: A 20 ml sample of venous blood was used for endothelial progenitor cell isolation. Samples were initially diluted with phosphate buffered saline (PBS) and peripheral blood mononuclear cells (PBMCs) were isolated by density gradient centrifugation using Ficoll-Paque™ PLUS (Amersham Pharmacia Biotech AB, Uppsala, Sweden). All isolations occurred within four hours of obtaining the sample. Recovered cells were washed twice with PBS and once in growth media consisting of Medium 199 (GIBCO BRL® Life Technologies) supplemented with 20% FBS, penicillin (100 U/ml) and streptomycin (100 μg/ml). Isolated cells were subsequently re-suspended in growth media and plated on dishes coated with human fibronectin (BIOCOAT® Becton Dickinson Labware, Bedford, Mass.) and incubated at 37° C. in humidified 5% $CO_2$. To eliminate the contamination of the assay with mature circulating endothelial cells, an initial pre-plating step was performed using 5 million PBMCs per well of a 6-well plate. After 48 hours, the non-adherent cells were collected and $1 \times 10^6$ cells were then re-plated onto fibronectin-coated 24-well plates for final colony number assessment. Growth media was changed every three days, and after seven days the numbers of endothelial progenitor cell colonies were counted. An endothelial progenitor cell colony consisted of multiple thin, flat cells emanating from a central cluster of rounded cells. A central cluster alone without associated emerging cells was not counted as positive. Colonies were counted manually in a minimum of four separate wells by observers unaware of the clinical profile.

Confirmation of endothelial lineage in selected subjects (n=10) was performed as previously described (Asahara et al., *Science* 275:964-967, 1997; Ito et al., *Cancer Res* 59:5875-5877, 1999). Briefly, indirect immunostaining was performed using endothelial specific antibodies directed against the Vascular Endothelial Growth Factor Receptor kinase insert domain receptor (KDR, Flk-1, vascular endothelial growth factor-2) and CD31 (DAKO). In addition, confirmation of the cell type was performed using uptake of DiI-acetylated low density lipoprotein (DiI-Ac-LDL) and co-staining with BS-1 Lectin. Further confirmation of EPC lineage was sought using flow cytometry by incubation of peripheral blood samples with monoclonal antibodies directed against KDR and the early stem and progenitor cell marker, AC133 (Miltenyi Biotech).

To assess reproducibility, colony counts were measured twice from the same subjects (n=10) from two separate blood samples, drawn at least one week apart and read independently by two observers blinded to the cardiovascular risk profile of the subject. The interobserver correlation for measurement of progenitor colonies was 0.92 while the intraclass correlation obtained by a single observer reading the same patient, sampled on two separate occasions separated by at least one week, was 0.97.

For measurement of cellular senescence, a subset of 16 age-matched patients who were divided into high and low Framingham risk groups (mean 7.3+/−2.3 versus 1.5+/−2.1; p<0.01) was recruited from the original 45 subjects. Endothelial progenitor cell cultures derived from these individuals were maintained for seven days with fresh media supplied every three days. Senescence associated β-galactosidase (SA-β-Gal) activity was measured as previously described in Dimri et al., *Proc. Natl. Acad. Sci. U.S.A.* 92:9363-9367, 1995. Briefly, cells were fixed with 4% formaldehyde and incubated overnight in X-Gal solution (1 mg/ml) at 37° C. without $CO_2$. Only isolated cells away from central colonies were analyzed and only those cells with distinct blue cytoplasmic color were counted as positive. The percentage of positive cells was determined by counting four random fields containing approximately 100-200 cells.

Assessment of endothelium-dependent and -independent function: Brachial reactivity testing was performed in the morning after an overnight fast. Imaging of the brachial artery, proximal to the antecubital fossa was performed using high-resolution ultrasound (12.5 MHz linear-array transducer ATL HDI 5000, Advanced Technology Laboratories, Inc. Bothell Wash.), as previously reported. (Prasad et al., *J Am Coll Cardiol* 38:1089-1095, 2001; Corretti et al., *J Am Coll Cardiol* 39:257-265, 2002.) Endothelium-dependent flow-mediated vasodilation (flow mediated brachial reactivity) was assessed by measuring the maximum increase in diameter of the brachial artery during reactive hyperemia created by a cuff inflated at 225 mmHg for five minutes on the upper arm, proximal to the measurement site. After rapid cuff deflation, flow velocity was measured for the first 15 seconds, and the artery lumen was imaged continually for the next 120 seconds of hyperemia. Baseline measurements included brachial artery diameter and flow velocity measured by pulse-wave-Doppler at approximately 70° to the vessel.

Following a rest period of 15 minutes, repeat baseline measurements (diameter and flow velocity) were recorded, followed by 0.4 mg sublingual nitroglycerin (nitroglycerin) spray to assess endothelium-independent vasodilation. Three minutes later, diameter and flow velocity measurements were recorded.

Studies were performed by a single experienced operator (G.Z.) and images were digitized and recorded on VHS videotape for subsequent analysis. Prior to patient enrollment in this study, an eight-week reproducibility study was performed of the entire procedure of flow-mediated and nitroglycerin induced brachial reactivity with a single observer and seven patients. Brachial artery diameter measurements at rest (3.77 and 3.72, r=0.99), with flow mediated dilation (4.02 and 4.0, r=0.97) and with nitroglycerin (4.23 and 4.09, r=0.88) were reproducible. Flow-mediated vasodilation was similar at baseline and at eight week follow up (12.7+/−0.8% and 11.9+/−0.8%, P=0.7). Furthermore, interobserver variability of the ultrasound analysis (acquired by a single operator) was also measured and was found to have an r value of 0.99. The brachial artery vasodilator response was calculated as:

%vasodilation=[post-ischemia or nitroglycerin diameter−baseline diameter]×100 baseline diameter Statistical analysis: Measurement data are expressed as mean±SEM. Means of subjects with high versus low cardiovascular risk were compared by 2-tailed unpaired Student's t-test. The chi-square test was used for comparisons of categorical variables. Univariate correlations were performed using the Spearman's correlation coefficient. To identify predictors of change in endothelial progenitor cell colony counts in a multivariate setting, multiple linear regression was used (General Linear Model Procedure of SAS) on the regressors: age, race, body mass index, cigarette smoking, hypertension, diabetes, cholesterol and glucose levels. In addition, the flow mediated brachial reactivity and nitroglycerin responses were also entered as covariates. A similar analysis was repeated for determinants of flow mediated brachial reactivity.

Example 2

Endothelial Progenitor Cell Colony Formation and Individual Risk Factors

Recent studies have defined a cell population termed endothelial progenitor cells that can be isolated from circulating mononuclear cells (Asahara et al., *Science* 275:964-967, 1997; Lin et al., *J Clin Invest* 105:71-77, 2000; Peichev et al., *Blood* 95:952-958, 2000), bone marrow (Reyes et al., *J Clin Invest* 109:337-346, 2002) and cord blood (Murohara et al., *J Clin Invest* 105:1527-1536, 2000).

As disclosed herein, tests have been conducted to determine that endothelial progenitor cells contribute to ongoing endothelial repair and maintenance of endothelial function. Endothelial progenitor cell activity in a group of healthy adult men has been measured. These individuals had no symptoms associated with atherosclerosis or of active ischemia and therefore seemed unlikely to have significant levels of ongoing neovascularization. The data described below shows that in these individuals, there is a strong association between depressed endothelial progenitor cell levels and impairment in endothelial function. In addition, individuals with high cardiovascular risk not only have fewer endothelial progenitor cells, but their endothelial progenitor cells also appear biologically older.

Peripheral blood mononuclear cells plated on fibronectin coated dishes formed distinct colonies that were easily visualized (FIG. 1). Endothelial progenitor cells isolated in this fashion exhibit many endothelial characteristics including staining positive for CD31, Tie-2 and Flk-1 (Asahara et al., *Science* 275:964-967, 1997; Ito et al., *Cancer Res* 59:5875-5877, 1999).

Figure 2:
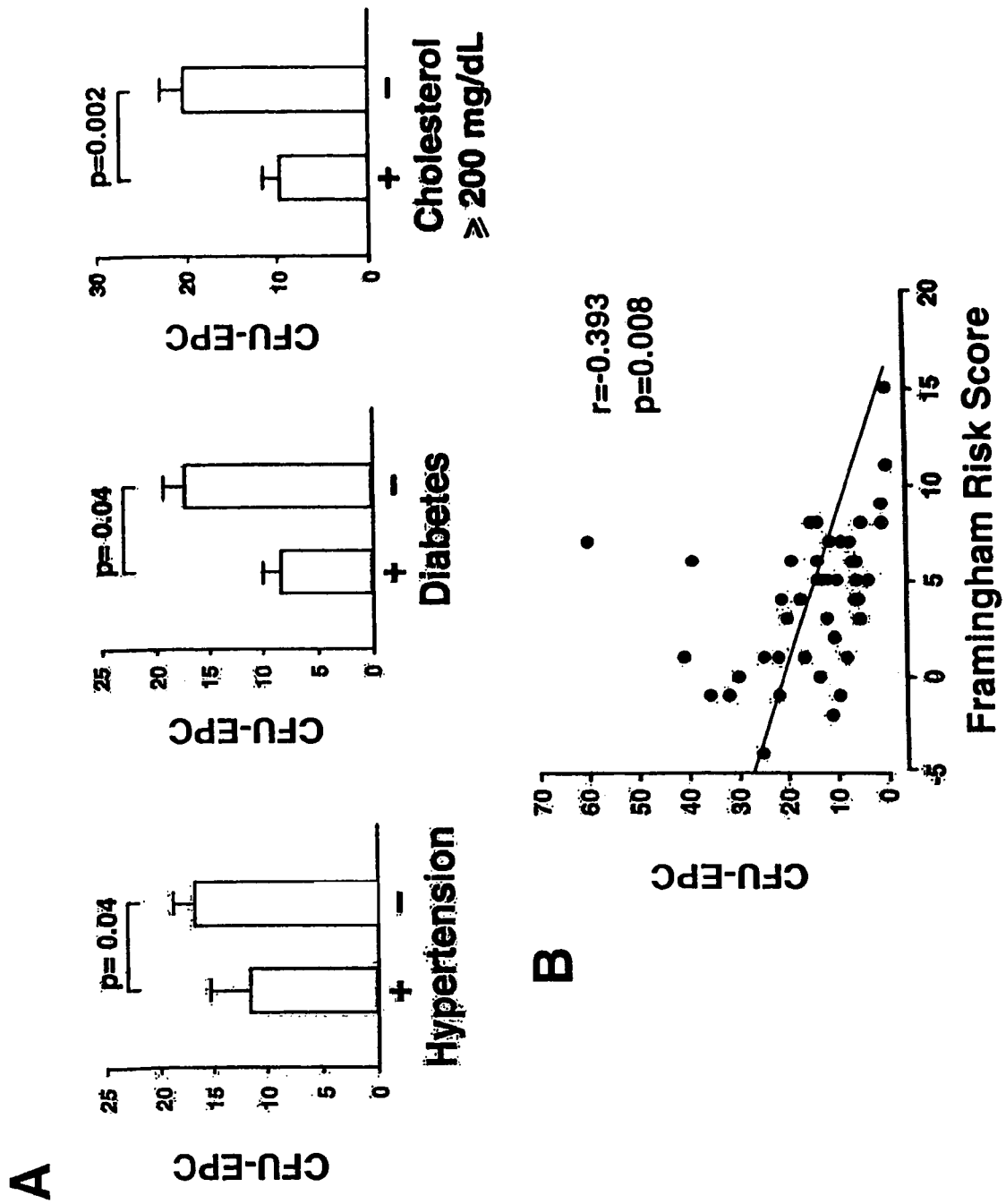
FIGS. 2A-B are a set of graphs showing association of cardiovascular risk factors on endothelial progenitor cell colony counts.

The level of circulating endothelial progenitor cells was assessed, and correlated with the presence or absence of known conventional cardiovascular risk factors. As noted in FIG. 2A, endothelial progenitor cell colony forming units were significantly reduced in patients with elevated serum cholesterol level, hypertension or diabetes (P=<0.05). A negative correlation between the patient's age and circulating endothelial progenitor cells was observed. However this relationship was not statistically significant. When, in this small group of relatively healthy volunteers, the individual risk factors of cholesterol, hypertension and diabetes were adjusted for age, only hypercholesterolemia remained significant (P=0.004, P=0.08 and P=0.07 respectively). To determine whether a cumulative risk factor profile influenced endothelial progenitor cell counts, the Framingham risk factor score was calculated for each patient. A significant correlation between the calculated risk score and endothelial progenitor cell counts (r=−0.39, p=0.008) was found, with higher scores associated with diminished endothelial progenitor cell counts (FIG. 2B).

Example 3

Figure 3:
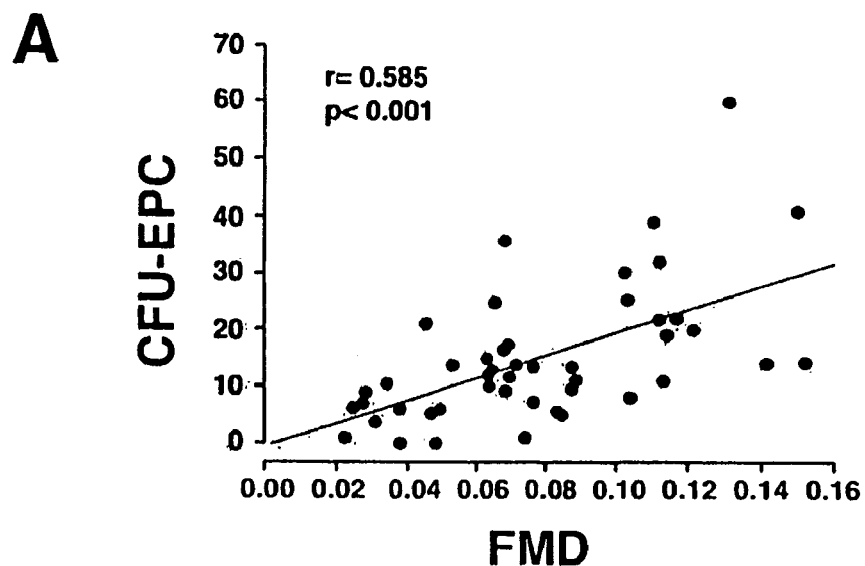
FIGS. 3A-C are a set of graphs showing the relationship between endothelial progenitor cell number and flow mediated brachial reactivity.
Figure 3:
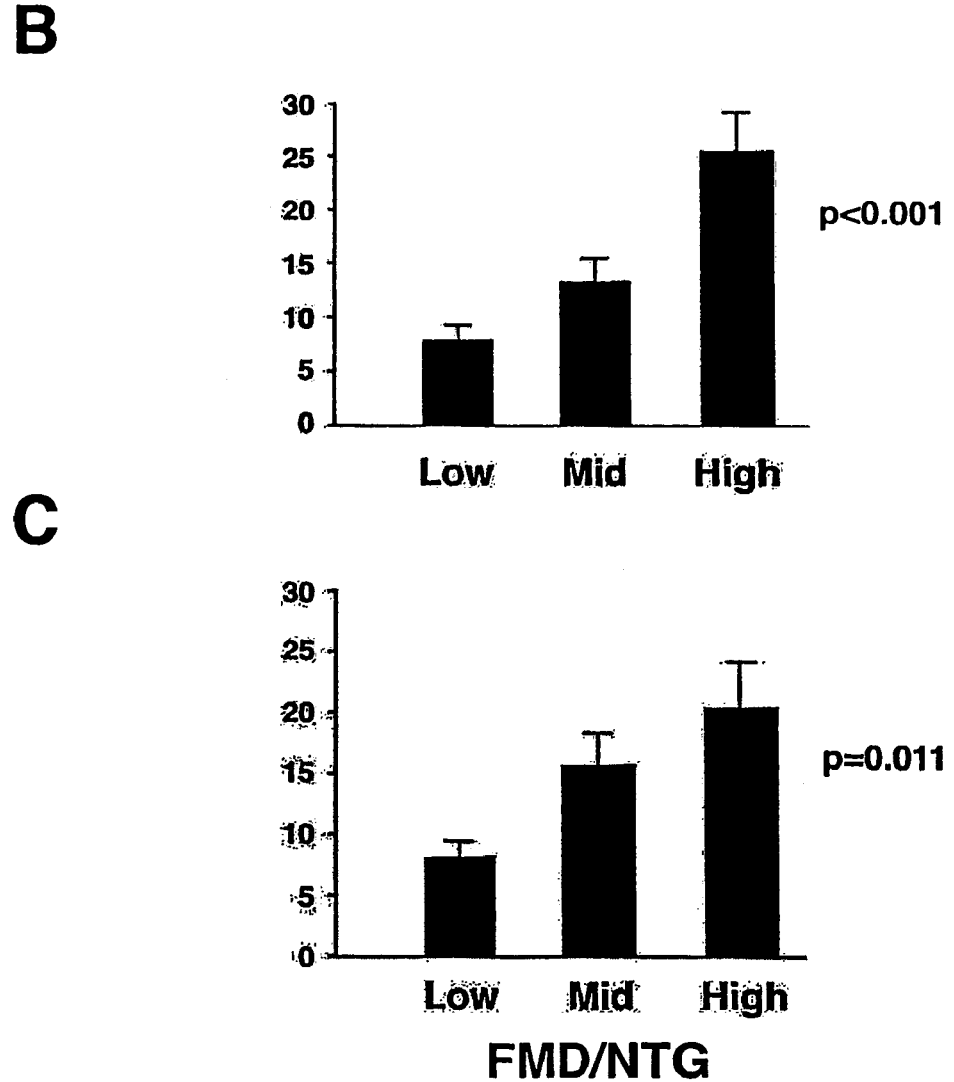

Endothelial Progenitor Cell Colony Counts and Endothelium-Dependent and -Independent Function Because the vascular endothelium integrates the injury from established and as yet unknown risk factors, the relationship between endothelial progenitor cell colony counts and flow mediated brachial reactivity, a composite measure of endothelial integrity, was assessed. As noted in FIG. 3A, there was a strong correlation between endothelial progenitor cell colony count and flow mediated brachial reactivity (r=0.59, P<0.001). When the measured flow mediated brachial reactivity was divided into tertiles (FIG. 3B), subjects with the highest flow mediated brachial reactivity had endothelial progenitor cell colony counts approximately 3-fold higher than those in the lowest tertile (24.5±3.6 versus 7.8±1.5, P<0.001).

In order to determine whether the relationship between endothelial progenitor cells and flow mediated brachial reactivity was strictly determined by endothelium-dependent function, the response of each subject to nitroglycerin was determined. These studies demonstrated a correlation between endothelial progenitor cell counts and the response to nitroglycerin (r=0.40, P=0.007). To assess whether the observed relationship between flow mediated brachial reactivity and endothelial progenitor cell counts were independent of vascular smooth muscle function, the ratio of flow mediated brachial reactivity/nitroglycerin was subsequently determined for each individual. This analysis normalizes endothelium-dependent responses for smooth muscle function in each patient. As demonstrated in FIG. 3C, patients in the tertile with the lowest flow mediated brachial reactivity/nitroglycerin ratio had reduced endothelial progenitor cell counts compared to those in the tertile with the highest flow mediated brachial reactivity/nitroglycerin ratio (8.1±1.2 versus 21.5±3.7, P=0.01).

Figure 5:
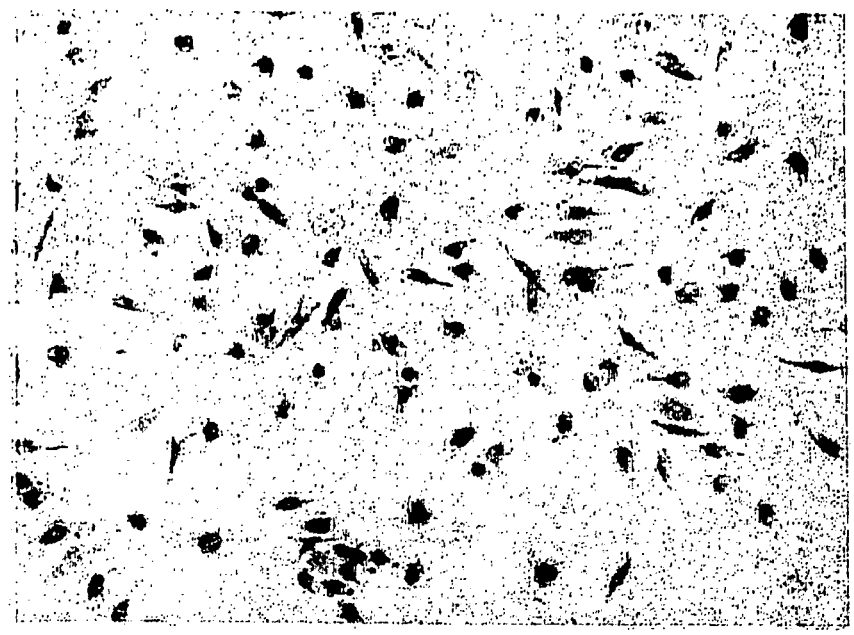
FIG. 5A-B show β-galactosidase activity in endothelial progenitor cells.
Figure 5:
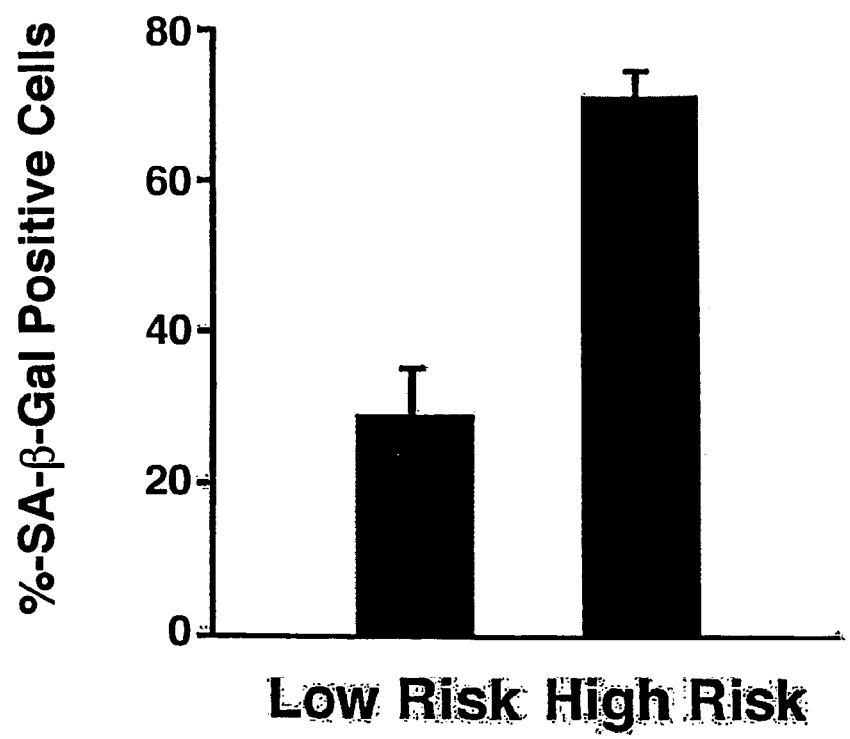

Finally, a multivariate regression analysis was performed to determine whether the number of endothelial progenitor cell colonies were associated with age, race, body mass index, cigarette smoking, hypertension, diabetes, total cholesterol, glucose levels, brachial flow mediated brachial reactivity or nitroglycerin responses. This analysis demonstrated that flow mediated brachial reactivity was an independent predictor of endothelial progenitor cell colony number (P<0.001). A reciprocal analysis that divided subjects into tertiles of measured endothelial progenitor cell activity demonstrated a striking relationship between endothelial progenitor cell levels and flow mediated brachial reactivity (FIG. 5, Table 1).

Example 4

Endothelial Progenitor Cells are Important Biological Determinants of Flow Mediated Brachial Reactivity If endothelial progenitor cells constitute an important aspect of ongoing vascular repair, it was reasoned that elevated levels of these cells might preserve flow mediated brachial reactivity even in the presence of ongoing vascular injury or dysfunction. Similarly, it was reasoned that in the setting of low levels of endothelial progenitor cells, flow mediated brachial reactivity might be impaired even in the absence of conventional risk factors. To test this hypothesis, subjects were divided into four subsets based on their Framingham score and endothelial progenitor cell colony counts. As noted in FIG. 4, those individuals with high endothelial progenitor cell counts (>13, mean 23) had preserved flow mediated brachial reactivity irrespective of whether or not they had a high or low conventional risk factor score. Similarly, those with low endothelial progenitor cell counts (<13, mean 7) had depressed flow mediated brachial reactivity, independent of whether or not their risk factor score was high or low. From these observations, it appears that endothelial progenitor cell activity is a better predictor of flow mediated brachial reactivity then the presence or absence of conventional risk factors. A formal statistical analysis was performed to confirm these conclusions. When assessed alone, Framingham risk score significantly correlated with observed flow mediated brachial reactivity (P=0.016). However, in a multivariate analysis of flow mediated brachial reactivity using both Framingham risk score and endothelial progenitor cells as regressors, cumulative risk score lost its significance (P=0.27), while endothelial progenitor counts were strongly significant (P=0.003) over and above the effects of the Framingham risk score.

Example 5

Risk Factor Profile and Endothelial Progenitor Cell Senescence

The decreased levels of circulating endothelial progenitor cells observed in individuals with elevated risk factors might occur through multiple mechanisms. Without being bound by theory, one possibility is that risk factors could somehow directly influence bone marrow mobilization or biological half-life of endothelial progenitor cells. Again, without being bound by theory, an alternative explanation is that with continuous endothelial damage or dysfunction there is an eventual exhaustion of the supply of endothelial progenitor cells. It is important to note that unlike multi-potential stem cells, progenitor cells do not share the almost infinite capacity for self-renewal. If the latter hypothesis was correct, endothelial progenitor cells derived from patient with high cardiovascular risk might be qualitatively different then endothelial progenitor cells derived from low risk patients. In particular, if endothelial progenitor cells from high risk individuals had undergone use-dependent depletion, those cells remaining in circulation might demonstrate in vitro characteristics of clonal exhaustion and/or accelerated aging.

To further assess this possibility, endogenous cellular β-galactosidase activity was measured, a widely used marker of cellular senescence (Dimri et al., *Proc. Natl. Acad. Sci. U.S.A.* 92:9363-9367, 1995) in a subset of our patients (n=16) selected because they had either high or low cumulative cardiovascular risk (Framingham risk 7.3+/−2.3 versus 1.5+/−2.1; ??p<0.01) but similar chronological age (high risk group mean age 49.1+/−5.9 versus low risk 54.6+/−9.3; p=0.85. Endothelial progenitor cells were grown from these subjects for seven days in culture and then assayed for the percentage of cells exhibiting a senescent phenotype. A significant difference in the observed level of cellular senescence that averaged 27+/−9% in low risk individuals compared to 72+/−15% in aged matched high risk individuals (P<0.001) was noted.

Figure 4:
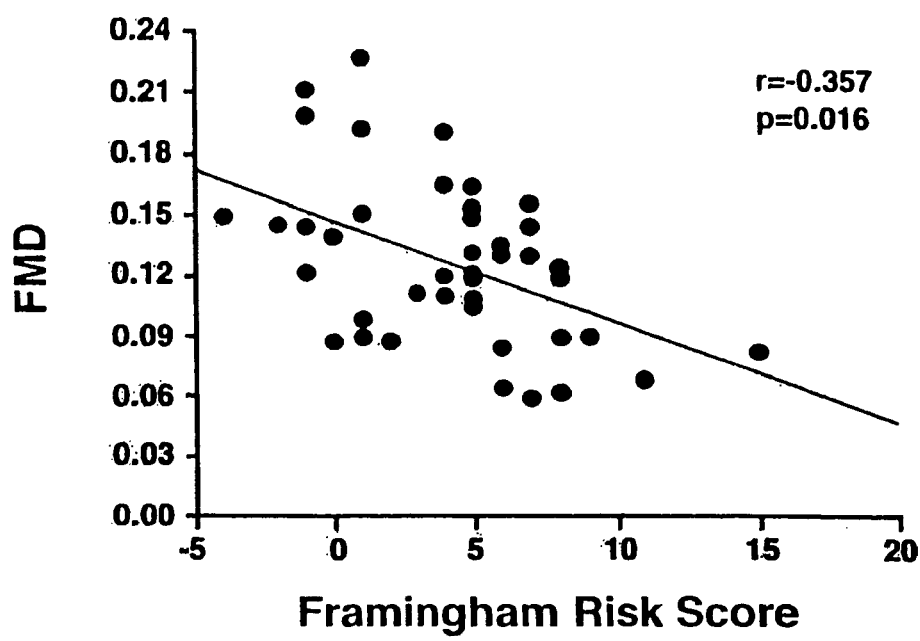
FIG. 4A-B is a set of graphs of endothelial progenitor cell activity is a predictor of flow mediated brachial reactivity. All subjects were divided into four subsets based on endothelial progenitor cell counts and Framingham risk factor score. Endothelial progenitor cell activity is a stronger predictor of measured flow mediated brachial reactivity than the presence or absence of conventional cardiovascular risks.
Figure 4:
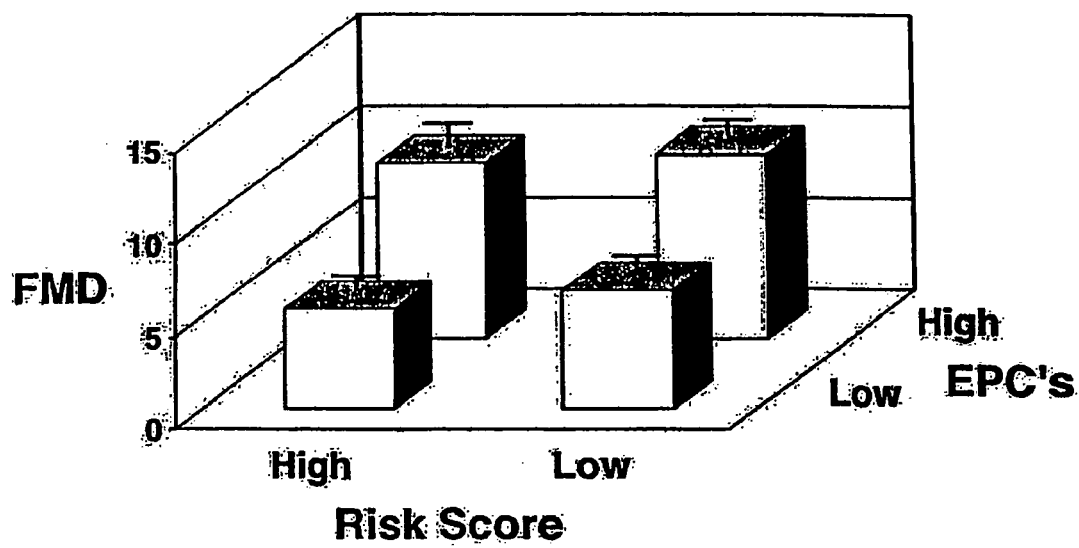

Endothelial damage ultimately represents a balance between the magnitude of injury and the capacity for repair. A variety of evidence suggests that cardiovascular risk factors induce endothelial injury and that impaired endothelial function represents a functional integration of this ongoing injury. As demonstrated herein, there is a strong correlation between levels of circulating endothelial progenitor cells and total cardiovascular risk. Levels of circulating endothelial progenitor cells were also highly correlated with endothelium-dependent flow mediated brachial reactivity. This observation suggests that individuals with multiple risk factors would develop impaired endothelial dysfunction when their intrinsic ability to repair the vascular endothelium was impaired (i.e. low endothelial progenitor cell levels). Analysis of the subgroup with multiple risk factors confirmed that flow mediated brachial reactivity was depressed only in those subjects with low endothelial progenitor cell counts, while a high risk factor score with high endothelial progenitor cell activity had preserved endothelial function (FIG. 4). These results are particularly significant given the growing realization that endothelial dysfunction conveys significant prognostic implications (Suwaidi et al., *Circulation* 101:948-954, 2000; Schächinger et al., *Circulation* 101:1899-1906, 2000; Perticone et al., *Circulation* 104:191-196, 2001; Gokce et al., *Circulation* 105:1567-1572, 2002; Halcox et al., *Circulation* 2002; 106:653-658). Similarly, as demonstrated herein, even in the absence of conventional risk factors, low levels of endothelial progenitor cells were predictive of impaired flow mediated brachial reactivity.

Without being bound by theory, one explanation for the observations of this latter subgroup is that impaired flow mediated brachial reactivity results from currently unknown and hence non-conventional risk factors influencing the vessel wall. Alternatively, impaired flow mediated brachial reactivity in this group might have resulted from a primary defect in endothelial progenitor cell levels. Indeed, although Framingham risk score was significantly correlated with flow mediated brachial reactivity, in a multivariate analysis of flow mediated brachial reactivity using both risk factor and endothelial progenitor cell as regressors, only endothelial progenitor cell levels remained a significant determinant of endothelial function.

Statin therapy increases the levels of circulating endothelial progenitor cells in both animal models as well as in patients with coronary artery disease (Llevadot et al., *J Clin Invest* 108:399-405, 2001; Dimmeler et al., *J of Clin Invest* 108:391-397, 2001; Vasa et al., *Circulation* 103:2885-2890, 2001). Thus, as described herein, lipid lowering agents, or other risk factor modifications, directly affect endothelial progenitor cell kinetics. Without being bound by theory, continuous endothelial damage or dysfunction there is an eventual depletion or exhaustion of a presumed finite supply of endothelial progenitor cells. Such depletion is not simply a reflection of chronological age, since as noted in FIG. 2A, although older subjects tended to have fewer endothelial progenitor cells, this relationship was not statistically significant. The level and duration of risk factors induced injury and dysfunction, and not biological age, is the primary determinant for the differences observed.

In the studies described herein, progenitor cells derived from high risk patients are both fewer in number and appear to undergo senescence at a more rapid rate then similar derived cells from low risk patients. Most of the emphasis in preventing cardiovascular disease has been aimed at reducing risk factor-induced endothelial damage or dysfunction, while comparatively little emphasis has been placed on understanding or manipulating the intrinsic vascular repair mechanisms. As described in this work, the endothelial progenitor cells are important in this ongoing repair process, as there is an association between circulating endothelial progenitor cells and both cardiovascular risk and function. Administration of endothelial cells could be used to prevent or treat loss of vascular function.

It will be apparent that the precise details of the methods or compositions described may be varied or modified without departing from the spirit of the described invention. We claim all such modifications and variations that fall within the scope and spirit of the claims below.

We claim:

1. A method of diagnosing decreased vascular function in a subject that does not have symptomatic cardiovascular disease, comprising
    selecting a subject that does not have symptomatic cardiovascular disease;
    assaying the number of endothelial progenitor cells in a blood sample from the subject;
    comparing the number of endothelial progenitor cells in the blood sample from the subject with a control, wherein the control is a number of endothelial progenitor cells in a blood sample from a control subject that does not have symptomatic cardiovascular disease and has a low Framingham Risk Score, and
    identifying a subject with decreased vascular function, wherein a decrease in the number of endothelial progenitor cells in the sample as compared to the control indicates decreased vascular function in the subject, and wherein vascular function is vascular contractility, brachial reactivity or a combination thereof.

2. The method of claim 1, wherein assaying the number of endothelial progenitor cells comprises
    isolating the buffy coat from a blood sample of the subject;
    isolating peripheral blood mononuclear cells from the buffy coat;
    culturing the peripheral blood mononuclear cells on a solid support coated with a first substrate, wherein cells from the peripheral blood mononuclear cells adhere to the first substrate;
    isolating non-adherent cells;
    culturing the non-adherent cells on a solid support coated with a second substrate, wherein a subset of the non-adherent cells adhere to the second substrate and form colonies;
    confirming that the subset of the non-adherent cells that adhered to the second substrate are endothelial progenitor cells by immunological assessment; and
    counting the number of colonies on the solid support,
    wherein the first substrate, or the second substrate, or both the first substrate and the second substrate comprise fibronectin, vitronectin, or collagen.

3. The method of claim 2, wherein a lower number of colonies on the solid support as compared to a control indicates decreased vascular function wherein vascular function is vascular contractility, brachial reactivity or a combination thereof.

4. The method of claim 1, wherein assaying the number of endothelial progenitor cells comprises
    determining the number of $VEGFR^{2+}CD31^{hi}$ cells in the sample.

5. The method of claim 1, wherein the control is a blood sample from a subject that does not have atherosclerosis.

6. The method of claim 1, wherein the control is a standard value.

7. The method of claim 2, wherein the first substrate comprises fibronectin.

8. The method of claim 2, wherein the first and the second substrate comprise fibronectin.

9. A method of diagnosing increased vascular function in a subject, comprising
    selecting a subject that does not have symptomatic cardiovascular disease;
    assaying a number of endothelial progenitor cells in first and second blood samples taken from the subject, wherein the second blood sample is taken from the subject after the first blood sample is taken from the subject;
    comparing the number of endothelial progenitor cells in the first blood sample with the number of endothelial progenitor cells in the second blood sample, and
    identifying a subject with increased vascular function, wherein an increase in the number of endothelial progenitor cells in the second blood sample as compared to the first blood sample indicates increased vascular function in the subject, wherein vascular function is vascular contractility, brachial reactivity or a combination thereof.

10. The method of claim 9, wherein the subject has been treated with a cholesterol-lowering agent.

11. The method of claim 10, wherein the first blood sample is a blood sample taken from the subject prior to treatment with the cholesterol-lowering agent.

12. The method of claim 9, wherein assaying the number of endothelial progenitor cells comprises
isolating the buffy coat from a blood sample of the subject;
isolating peripheral blood mononuclear cells from the buffy coat;
culturing the peripheral blood mononuclear cells on a solid support coated with a first substrate, wherein cells from the peripheral blood mononuclear cells adhere to the first substrate;
isolating non-adherent cells that do not adhere to the first substrate;
culturing the non-adherent cells on a solid support coated with a second substrate, wherein a subset of the non-adherent cells adhere to the second substrate and form colonies;
confirming that the subset of the non-adherent cells that adhered to the second substrate are endothelial progenitor cells; and
counting the number of colonies on the solid support,
wherein the first substrate, or the second substrate, or both the first substrate and the second substrate comprise fibronectin, vitronectin, or collagen.

13. The method of claim 12, wherein a higher number of colonies on the solid support as compared to a control indicates increased vascular function, wherein vascular function is vascular contractility, brachial reactivity or a combination thereof.

14. The method of claim 12, wherein the first substrate comprises fibronectin.

15. The method of claim 12, wherein the first substrate and the second substrate comprises fibronectin.

16. The method of claim 9, wherein assaying the number of endothelial progenitor cells comprises
determining the number of $VEGFR^{2+}CD31^{hi}$ cells in the sample.

17. A method of diagnosing increased cardiovascular risk or decreased vascular function in a subject, comprising
selecting a subject that does not have symptomatic cardiovascular disease;
assaying a number of senescent endothelial progenitor cells in a blood sample from the subject, wherein a senescent endothelial progenitor cell is a viable endothelial cell that exhibits clonal exhaustion in vitro;
comparing the number of senescent endothelial progenitor cells in the blood sample from the subject with a control, wherein the control is a number of senescent endothelial progenitor cells in a blood sample from a control subject that does not have symptomatic cardiovascular disease and has a low Framingham Risk Score, and
identifying a subject with increased cardiovascular risk or decreased vascular function, wherein an increase in the number of senescent endothelial progenitor cells in the sample as compared to the control indicates increased cardiovascular risk or decreased vascular function.

18. The method of claim 17, wherein the control is a standard value.

19. The method of claim 17, wherein the control is a number of senescent endothelial progenitor cells in a blood sample from a subject known not to be affected by a disease or disorder.

20. The method of claim 17, wherein vascular function comprises vascular contractility, brachial reactivity, atrierial hyperplasia, or a combination thereof.

21. The method of claim 1, wherein the control subject has a Framingham Risk Score of less than 1.5.

22. The method of claim 2, wherein confirming that the subset of the non-adherent cells that adhere to the second substrate are endothelial progenitor cells by immunological assessment comprises contacting the cells with antibodies that specifically bind Vascular Endothelial Growth Factor Receptor kinase insert domain receptor, contacting the cells with antibodies that specifically bind CD31, or measuring uptake of DiI-acetylated low density lipoprotein and co-staining with BS-1 Lectin.

23. The method of claim 12, wherein confirming that the subset of the non-adherent cells that adhere to the second substrate are endothelial progenitor cells comprises immunostaining with antibodies that specifically bind Vascular Endothelial Growth Factor Receptor kinase insert domain receptor; contacting the cells with antibodies that specifically bind CD31; or measuring uptake of DiI-acetylated low density lipoprotein followed by co-staining with BS-1 Lectin.

24. The method of claim 17, wherein the control subject has a Framingham Risk Score of less than 1.5.

25. The method of claim 17, assaying a number of senescent endothelial progenitor cells comprises measuring endogenous beta-galactosidase.

* * * * *

UNITED STATES PATENT AND TRADEMARK OFFICE
CERTIFICATE OF CORRECTION

PATENT NO. : 7,708,977 B2  Page 1 of 1
APPLICATION NO. : 10/534626
DATED : May 4, 2010
INVENTOR(S) : Finkel et al.

It is certified that error appears in the above-identified patent and that said Letters Patent is hereby corrected as shown below:

Column/Line: 19/55-56

Error: % vasodilation =[post-ischemia or nitroglycerin diameter – baseline diameter] X 100
baseline diameter

Should read: % vasodilation =[post-ischemia or nitroglycerin diameter – baseline diameter] X 100
baseline diameter Signed and Sealed this Twenty-third Day of November, 2010

David J. Kappos
*Director of the United States Patent and Trademark Office*